United States Patent [19]

Hunt

[11] 4,275,067
[45] Jun. 23, 1981

[54] DECARBOXYCLAVULANIC ACID THIO ETHERS, THEIR PREPARATION AND USE

[75] Inventor: Eric Hunt, Betchworth, England

[73] Assignee: Beecham Group Limited, England

[21] Appl. No.: 932,489

[22] Filed: Aug. 10, 1978

[30] Foreign Application Priority Data

Sep. 14, 1977 [GB] United Kingdom ............... 38286/77

[51] Int. Cl.³ .................... C07D 498/04; A61K 31/42
[52] U.S. Cl. ................................ 424/263; 260/245.3; 424/246; 424/271; 424/272; 542/413; 542/416
[58] Field of Search ...................... 542/413, 416, 427; 260/307 FA, 294.8 C, 245.3; 424/272, 271, 246, 263, 272

[56] References Cited

U.S. PATENT DOCUMENTS 4,093,626  6/1978  Hunt ............................. 260/307 FA Primary Examiner—Mark L. Berch Attorney, Agent, or Firm—Jacobs & Jacobs

[57] ABSTRACT

Compounds of the formula (II):

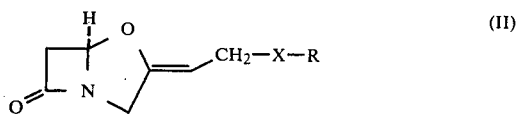

wherein X is S, SO or $SO_2$; and R is (a) an alkyl group of up to 4 carbon atoms, (b) an alkyl group of up to 4 carbon atoms substituted by an $OR^1$, $NHR^1$, $NH.CO.R^1$ or $CO_2R^2$ group wherein $R^1$ is a hydrogen atoms, an alkyl group of up to 4 carbon atoms or benzyl group, and $R^2$ is a moiety such that $CO_2R^2$ is a carboxyl, salted carboxyl or esterified carboxyl group, (c) an aryl group or (d) an aralkyl group are useful for their antifungal and $\beta$-lactamase inhibitory properties.

52 Claims, No Drawings

DECARBOXYCLAVULANIC ACID THIO ETHERS, THEIR PREPARATION AND USE

The present invention relates to novel compounds having anti-fungal and β-lactamase inhibitory activity, to the process for their preparation and to pharmaceutical compositions containing them.

Belgian Pat. No. 827926 discloses that clavulanic acid, which is the compound of the formula (I):

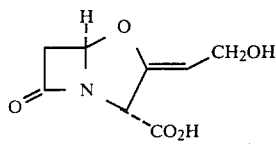

and its salts and esters are able to enhance the effectiveness of penicillins and cephalosporins by virtue of their ability to inhibit β-lactamase. We have now discovered a new group of β-lactam compounds that are also able to enhance the effectiveness of penicillins and cephalosporins, and which have anti-fungal activity.

The present invention provides the compounds of the formula (II):

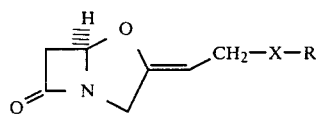

wherein X is S, SO or $SO_2$; and R is (a) an alkyl group of up to 4 carbon atoms, (b) an alkyl group of up to 4 carbon atoms substituted by an $OR^1$, $NHR^1$, $NH.CO.R^1$ or $CO_2R^2$ group wherein $R^1$ is a hydrogen atom, an alkyl group of up to 4 carbon atoms or benzyl group, and $R^2$ is a moiety such that $CO_2R^2$ is a carboxyl, salted carboxyl or esterified carboxyl group, (c) an aryl group or (d) an aralkyl group.

When used herein the term "aryl" means a phenyl, thienyl, furyl or pyridyl group or a phenyl group substituted by fluorine, chlorine, bromine, methyl or $OR^1$, $NHR^1$, $NH.CO.R^1$ or $CO_2R^2$ group where $R^1$ and $R^2$ are as defined above. When used herein the term "aralkyl" means an alkyl group substituted by an aryl group.

Suitable groups R include those of the sub-formulae (a)-(c):

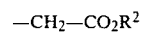 (a)

 (b)

 (c)

wherein $R^2$ is as defined in relation to formula (I); $R^3$ is a $OR^1$, $NHR^1$, $NH.CO.R^1$ or $CO_2R^2$ group wherein $R^1$ and $R^2$ are as defined in relation to formula (I); and $R^4$ is an aryl group.

Most suitably $R^2$ is a salting ion (e.g. a lithium, sodium, potassium, calcium, magnesium, ammonium, trimethylammonium, pyrrolidinium or the like ion) or an alkyl group of up to 4 carbon atoms or a benzyl group.

Most suitably $R^1$ is a hydrogen atom or a methyl group.

Most suitably $R^4$ is a phenyl, pyridyl, furyl or thienyl group.

Thus R may be a methyl, ethyl, n-propyl, n-butyl, benzyl, phenyl, methoxyphenyl, methoxybenzyl or like group.

Most suitably R is a phenyl or substituted phenyl group.

Further suitable groups R are methyl, ethyl, or propyl.

The skilled man will realise that any substituents on the group R will be selected so that they do not interfere with the preparation hereinafter described. For example, R will not be an alkyl group substituted at the α-carbon atom by an $OR^1$ or $NHR^1$ group.

The present invention also provides a process for the preparation of the compounds of the formula (II) which process comprises the reaction of the compound of the formula (III):

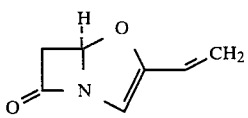

with a thiol of the formula (IV):

  (IV)

wherein R is as defined in relation to formula (II); and thereafter if desired oxidizing the resulting sulphide to a sulphoxide or sulphone.

For those compounds where R contains a $NHR^1$ group, the amino group will normally be protected during the addition reaction, for example, with a benzyl- or p-nitrobenzyloxycarbonyl group which is subsequently removed by hydrogenation.

The addition reaction will normally be performed in the presence of a free radical initiator such as an azonitrile or oxygen or a peroxide or by irradiation with ultraviolet radiation, X-rays or the like.

The process of this invention may be conducted without solvent or, more suitably, in the presence of an inert solvent such as tetrahydrofuran, 1,2-dimethoxyethane or the like.

The temperature at which the reaction is effected is to some extent governed by the method used for the production of the free radicals. Thus if ultraviolet radiation is employed a temperature at or below room temperature can be used (for example −80° C. to 30° C.). If an azonitrile is being used the temperature will be somewhat higher as useful azonitriles such as α,α'-azoisobutyronitrile do not generally decompose to produce radicals below 40° C.

The compounds of the formula (II) wherein X is S may be converted to the corresponding compound wherein X is SO or $SO_2$ by oxidation in an inert solvent. Suitable oxidization agents include per-acids such as perbenzoic acid or m-chloroperbenzoic acid. Suitable solvents for such reactions include methylene chloride, tetrahydrofuran or the like. In general a mixture of the sulphone and the sulphoxide is produced although increasing the proportion of the oxidizing agent tends to increase the proportion of the more highly oxidized product. The sulphoxide and sulphones may be separated chromatographically, for example using ethyl acetate/petrol mixtures and silica gel.

The compound of formula (III) may be prepared by the reaction of N,N-dimethylformamide dimethylacetal and clavulanic acid in dry tetrahydrofuran at room temperature. The compound of the formula (III) may be isolated but in general it is more convenient to use it in-situ.

The present invention also provides a pharmaceutical composition which comprises a compound of the formula (II) and a carrier therefor.

Such compositions may be used as anti-fungal compositions or may be used in the treatment of bacterial infections.

Compositions for use in the treatment of bacterial infections which contain a compound of the formula (II) as sole active ingredient will be used for concurrent administration with a penicillin or cephalosporin since the compounds of the formula (II) possess no significant antibacterial activity.

The anti-bacterial compositions of the invention include those in a form adapted for oral, topical or parenteral use and may be used in the treatment of infection in mammals including humans.

Suitable forms of the compositions of this invention include tablets, capsules, creams, syrups, suspensions, solutions, reconstitutable powders and sterile forms suitable for injection or infusion. Such compositions may contain conventional pharmaceutically acceptable materials such as diluents, binders, colours, flavours, preservatives, disintegrants and the like in accordance with conventional pharmaceutical practice in the manner well understood by those skilled in the art of formulating antibiotics.

Injectable or infusable compositions of a compound of the formula (II) are one preferred composition aspect of this invention.

Unit dose compositions comprising a compound of the formula (II) adapted for oral administration form a preferred composition aspect of this invention.

The compound of the formula (II) may preferably be present together with a β-lactam antibiotic. Suitable β-lactam antibiotics for inclusion in the compositions of this invention include benzylpenicillin, phenoxymethylpenicillin, carbenicillin, azidocillin, propicillin, ampicillin, amoxycillin, epicillin, ticarcillin, cyclacillin, cefatriazine, pirbenicillin, α-sulphonyloxybenzylpenicillin, cephaloridine, cephalothin, cefazolin, cephalexin, cefoxitin, cephacetrile, cephamandolenafate, cephapirin, cephradine, 4-hydroxy-cephalexin, cefaparole, cephaloglycine, and other well known penicillins and cephalosporins or pro-drugs therefor such as hetacillin, metampicillin, 4-acetoxyampicillin, the acetoxymethyl, ethoxycarbonyloxymethyl, pivaloyloxymethyl or phthalidyl esters of benzylpenicillin, ampicillin, amoxycillin or cephaloglycine or the phenyl, tolyl or indanyl α-esters of carbenicillin or ticarcillin or the like. Such compounds are frequently used in the form of a salt or hydrate.

Naturally if the penicillin or cephalosporin present in the composition is not suitable for oral administration then the composition will be adapted for parenteral administration.

When present in an pharmaceutical composition together with a β-lactam antibiotic, the ratio of a compound of the formula (II) present to β-lactam antibiotic present may vary over a wide range of ratios, for example 3:1 to 1:3 and advantageously may be from 2:1 to 1:2, for example, 1:1.

The total quantity of antibacterial agents present in any unit dosage form will normally be between 50 and 1500 mg and will usually be between 100 and 1000 mg.

Compositions of this invention may be used for the treatment of infections on inter alia, the respiratory tract, the urinary tract and soft tissues and mastitis in cattle.

Normally between 50 and 3000 mg of the compounds of the invention will be administred each day of treatment but more usually between 100 and 1000 mg of the compounds of the invention will be administered per day, for example as 1–6 doses, more usually 2–4 doses.

The penicillin or cephalosporin in synergistic compositions of this invention will normally be present by up to or at approximately the amount at which it is conventionally used.

Particularly favoured compositions of this invention will contain from 150–1000 mg of amoxycillin, ampicillin or a pro-drug therefor and from 50–500 mg of a compound of the formula (II) and more suitably from 200–500 mg of amoxycillin, ampicillin or a pro-drug therefor and from 50–250 mg of a compound of the formula (II).

The anti-fungal compositions according to the invention will be adapted for oral, topical, rectal, intravaginal or parenteral administration. Such compositions may be used together with other medicinal agents. The compositions may be formulated in conventional manner. Thus, for example formulations for external applications may be prepared in oily, aqueous or powdered media in the form of conventional skin paints, lotions, creams, ointments, aerosols or dusting powders.

The anti-fungal compositions according to the invention preferably contain the active material at a concentration of 0.1 to 95% by weight, advantageously 0.5 to 40%.

The following Examples illustrate the invention.

EXAMPLE 1

(Z, 5R)-3-(2-Phenylthioethylidene)-4-oxa-1-azabicyclo[3.2.0]heptan-7-one

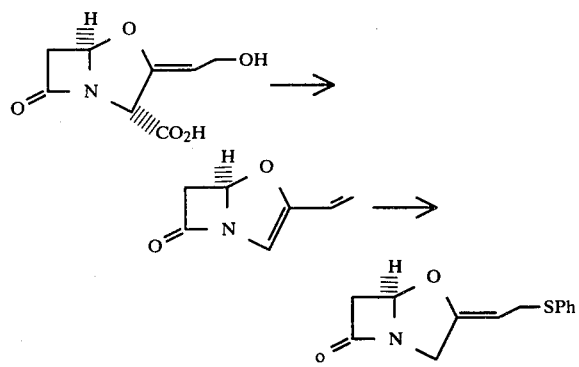

A solution of clavulanic acid (3.0 mmole) in dry tetrahydrofuran (10 ml) and a solution of N,N-dimethylformamide dimethylacetal (3.5 mmole) in dry tetrahydrofuran (10 ml) were added simultaneously to dry tetrahydrofuran (20 ml) which was being stirred rapidly at room temperature. After addition was complete (5 minutes), the resulting mixture was decolourised using charcoal (0.5 g) and filtered, the filter being washed well with fresh tetrahydrofuran. The combined filtrate and washings were concentrated to 10 ml. by evaporation of solvent under reduced pressure to give a solution containing (5R)-7-oxo-3-vinyl-4-oxa-1-azabicyclo[3.2.0]-hept-2-ene (ca 2.5 moles).

To the above solution, thiophenol (0.4 ml.) and αα′-azoisobutyronitrile (10 mg) were added and the resulting mixture was stirred under dry nitrogen at 50° for 2 hours. The solvent was evaporated under reduced pressure and the resulting residue was chromatographed on silica gel (20 g) using ethyl acetate/petroleum ether (b.p. 60°–80°). The title compound was thus obtained as a colourless oil (143 mg., 0.58 mmole), $[\alpha]_D^{25} = +73.2°$ (c=1.0, CHCl$_3$) $\nu_{max}$ (CHCl$_3$): 1793 (β-lactam C=O), 1697 (olefinic C=C)cm$^{-1}$. δ(CDCl$_3$): 2.79 (d, J 16 Hz, 1H, C(6)H), 3.30 (dd, J 16, 2 Hz, 1H, C(6)H), 3.47 (d, J 16 Hz, 1H, C(2)H), 3.58 (d, J 7 Hz, 2H, CH$_2$S), 4.27 (d, J 16 Hz, 1H, C(2)H), 4.42 (t, J 7 Hz, 1H, olefinic H), 5.33 (d, J 2 Hz, 1H, C(5)H), 7.05–7.40 (m, 5H, aromatic H).

The title compound inhibited β-lactamase enzymes as shown in the following Table. I$_{50}$ values were determined using the process described in Belgian Pat. No. 827,926.

| Source of β-lactamase | I$_{50}$ (μg/ml) |
|---|---|
| Enterobacter cloacae P 99 | 1.32 |
| Pseudomonas aeruginosa A | 2.2 |
| Proteus mirabilis C 889 | 4.4 |
| E. coli JT 4 | 0.36 |
| Ps. aeruginosa Dalgleish | 0.60 |
| Staph. aureus Russell | 0.25 |

EXAMPLE 2

(Z, 5R)-3-(2-Phenylsulphonylethylidene)-4-oxa-1-azabicyclo[3.2.0]heptan-7-one and (Z, 5R)-3-(2-phenylsulphinylethylidene)-4-oxa-1-azabicyclo[3.2.0]heptan-7-one

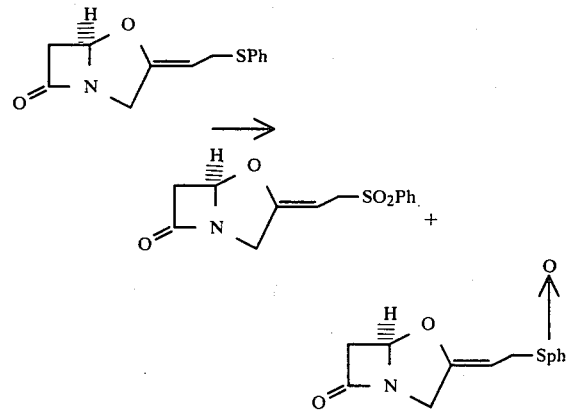

(Z, 5R)-3-(2-Phenylthioethylidene)-4-oxa-1-azabicyclo[3.2.0]heptan-7-one (125 mg., 0.5 mmole) was dissolved in dry methylene dichloride (10 ml) and the solution was stirred and ice-cooled while m-chloroperbenzoic acid (115 mg., 0.67 mmole) in dry methylene dichloride (4 ml) was added dropwise with exclusion of moisture. After addition was complete (5 minutes), the mixture was stirred and ice-cooled for a further 25 minutes. The mixture was diluted with ethyl acetate (50 ml) and washed once with saturated sodium bicarbonate solution (10 ml) and once with saturated brine (10 ml). The solution was dried (magnesium sulphate) and the solvent was evaporated under reduced pressure to yield a colourless gum (150 mg). The gum was chromatographed on silica gel (15 g) using ethyl acetate/petroleum ether (b.p. 60°–80°) to give, in order of elution, (Z, 5R)-3-(2-phenyl-sulphonylethylidene)-4-oxa-1-azabicyclo-[3.2.0] heptan-7-one as colourless crystals (40 mg) and (Z, 5R)3-(2-phenylsulphinylethylidene)-4-oxa-1-azabicyclo[3.2.0]heptan-7-one as a colourless gum (38 mg)(this material appears to be a 1:1 mixture of compounds which are isomeric at the sulphur atom).

The sulphone was characterised by the following: $[\alpha]_D^{24} = +114.6°$ (c=1.0, CHCl$_3$). $\nu_{max}$ (CHCl$_3$): 1797 (β-lactam C=O), 1700 (olefinic C=C), 1320 and 1150 (sulphone)cm$^{-1}$. δ(CDCl$_3$): 2.46 (d, J 16 Hz, 1H, C(6)H), 3.23 (dd, J 16, 2 Hz, 1H, C(6)H), 3.46 (d, J 15 Hz, 1H, C(2)H), 3.84 (d. J 7 Hz, 2H, CH$_2$SO$_2$), 4.28 (d, J 15 Hz, 1H, C(2)H), 4.43 (t, J 7 Hz, 1H, olefinic H), 5.18 (d, J 2 Hz, 1H, C(5)H), 7.35–7.65 (m, 3H, aromatic H), 7.85 (dd, J 7, 2 Hz, 2H, aromatic H).

The sulphoxide was characterised by the following: $[\alpha]_D^{24} = 109.3°$ (c=1.0, CHCl$_3$). $\nu_{max}$ (CHCl$_3$): 1800, (β-lactam C=O), 1698 (olefinic C=C), 1040 (sulphoxide)cm$^{-1}$. δ(CDCl$_3$): 2.65 and 2.68 (both d, J 16 Hz, 1H, C(6)H), 3.1–3.8 (complex, 4H, C(6)H, C(2)H, CH$_2$SO), 4.15–4.45 (complex 2H, C(2)H, olefinic H), 5.25 (m, 1H, C(5)H), 7.46 (br.s, 5H, aromatic H).

EXAMPLE 3

(Z, 5R)-3-(2-Ethylthioethylidene)-4-oxa-1-azabicyclo[3.2.0]-heptan-7-one

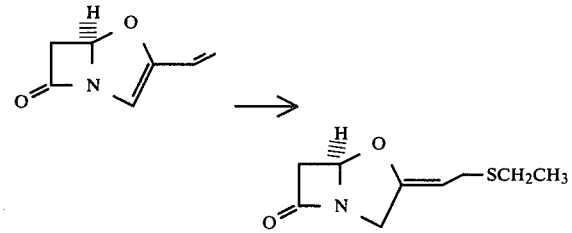

(5R)-7-Oxo-3-vinyl-4-oxa-1-azabicyclo[3.2.0]hept-2-ene in dry tetrahydrofuran (10 ml) was obtained from clavulanic acid (3.0 mmole) using the process described in Example 1. To this solution ethane thiol (0.5 ml) and αα′-azoisobutyronitrile (10 mg) were added and the mixture was stirred at 50° under a dry nitrogen atmosphere for 24 hrs. The solvent was evaporated under reduced pressure and the resulting residue was chromatographed on silica gel (15 g) using ethyl acetate/petroleum ether. The title compound was thus obtained as a colourless oil (25 mg), $[\alpha]_D^{23} = +77.1°$ (c=1.25, CHCl$_3$). (Found: M$^{30}$, 199.0676; C$_9$H$_{13}$NO$_2$S requires 199.0667); $\nu_{max}$ (CHCl$_3$): 1793 (β-lactam C=O), 1700 (olefinic C=C)cm$^{-1}$; δ(CDCl$_3$): 1.23 (t, J 7 Hz, 3H, CH$_3$), 2.48 (q, J 7 Hz, 2H, SCH$_2$), 2.93 (d, J 17 Hz, 1H, C(6)H), 3.15–3.65 (complex, 4H, C(6)H, C(2)H, =CCH$_2$S), 4.25–4.50 (complex, 2H, C(2)H, olefinic H), 5.45 (d, J 2 Hz, 1H, C(5)H); m/e: 199 (M$^+$, 5%), 138 (47), 96 (100).

EXAMPLE 4

(Z, 5R)-3-(2-Ethylthioethylidene)-4-oxa-1-azabicyclo[3.2.0]-heptan-7-one.

(5R)-7-Oxo-3-vinyl-4-oxa-1-azabicyclo[3.2.0]hept-2-ene (320 mg) was dissolved in dry toluene (100 ml) and ethane thiol (0.5 ml) was added to the solution. The mixture was purged with dry nitrogen and was then irradiated using a medium pressure mercury lamp at room temperatures for 1 hour. The solvent was removed under reduced pressure and the residue was chromatographed on silica gel (15 g) using ethyl acetate/petroleum ether. The title compound was thus obtained as a colourless oil (6 mg) and had spectroscopic properties identical to those described in Example 3.

EXAMPLE 5

Antibacterial synergy

The compounds from Examples 1 and 2 were active as antibacterial synergists when combined with ampicillin as detailed in the following Table.

| R | Concentration of Inhibitor ($\mu$g/ml) | MIC ($\mu$g/ml) for ampicillin | |
|---|---|---|---|
| | | *Staph. aureus* Russell | *Klebsiella aerogenes* E70 |
| SC$_6$H$_5$ | — | 250 | 125 |
| | 5 | 0.04 | |
| | 1 | 0.15 | |
| SO$_2$C$_6$H$_5$ | 5 | 0.15 | 12.5 |
| | 1 | 1.25 | |
| SOC$_6$H$_5$ | 5 | 0.6 | 12.5 |

The three inhibitors described in the above Table were all essentially inactive (MIC ≧ 500 $\mu$g/ml) as antibacterials against *Staphylococcus aureus* Russell and *Klebsiella aerogenes* E70.

EXAMPLE 6

(Z)-(5R)-3-[2-(Methoxycarbonylmethylthio)ethylidene]-4-oxa-1-azabicyclo[3.2.0] heptan-7-one

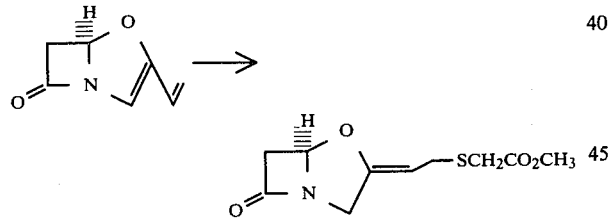

(5R)-7-Oxo-3-vinyl-4-oxa-1-azabicyclo[3.2.0]hept-2-ene (ca 2.5 mmole) in tetrahydrofuran (20 ml) was prepared from clavulanic acid (3.0 mmole) as described in Example 1.

To the above solution, methyl thioglycolate (0.4 g) and benzoyl peroxide (10 mg) were added. The mixture was stirred at 40° under a dry nitrogen atmosphere while being irradiated by a 60 W bulb placed 1″ from the flask for a total of 11 hours. The mixture was then diluted with ethyl acetate (100 ml) and was washed with saturated sodium bicarbonate solution (20 ml) and water (50 ml). The solution was dried (magnesium sulphate) and the solvent was evaporated under reduced sulphate) and the solvent was evaporated under reduced pressure to yield a yellow gum. The gum was chromatographed on silica gel (15 g) using graded elution from 1:6 to 1:2 ethyl acetate/petroleum ether (b.p. 60°–80°). The title compound was thus obtained as a colourless gum (46 mg), $[\alpha]_D^{22} = +49.5°$. (c 1.0, CHCl$_3$), (Found: M$^+$, 243.0567; C$_{10}$H$_{13}$NO$_4$S requires 243.0565). $\nu_{max}$ (CHCl$_3$): 1795, 1735, 1700 cm$^{-1}$. m/e: 243 (M$^+$, 5%), 170 (6), 138 (38), 96 (100).

EXAMPLE 7

(Z)-(5R)-3-[2-(2-Methoxycarbonylethylthio)ethylidene]-4-oxa-1-azabicyclo[3.2.0]hetpan-7-one (5R)-7-Oxo-3-vinyl-4-oxa-1-azabicyclo[3.2.0]hept-2-ene (2.6mmole) and methyl 3-mercaptopropionate (0.8 ml) were converted into the tital compound using the process described in Example 6. The title compound was obtained as a colourless gum (73 mg), $[\alpha]_D^{22} = +52.8°$ (c 1.0, CHCl$_3$), (Found: M$^+$, 257.0728; C$_{11}$H$_{15}$NO$_4$S requires 257.0722). $\nu_{max}$ (CHCl$_3$): 1790, 1730, 1700 cm$^{-1}$. m/e 257 (M$^+$, 1%), 188 (8), 138 (75), 96 (100).

EXAMPLE 8

(Z)-(5R)-3-[2-(2-Hydroxyethylthio)ethylidene]-4-oxa-1-azabicyclo[3.2.0]heptan-7-one (5R)-7-Oxo-3-vinyl-4-oxa-1-azabicyclo[3.2.0] hept-2-ene (2.5 mmole) in dry tetrahydrofuran (20 ml) was treated with 2-mercaptoethanol (0.4 ml) and benzoyl peroxide (10 mg). The resulting mixture was stirred under dry nitrogen while being irradiated using a 200 W bulb placed 1″ from the reaction vessel for a total time of 14 hours. The mixture was diluted with ethyl acetate (100 ml) and was washed with saturated sodium bicarbonate solution and saturated brine. The solution was dried (magnesium sulphate) and the solvent was evaporated under reduced pressure to give a yellow oil. The oil was chromatographed on silica gel (20 g) using graded elution from 1:4 to 1:1 ethyl acetate/petroleum ether (b.p. 60°–80°). The title compound was thus obtained as a colourless gum (45 mg), $[\alpha]_D^{22} = +66.8°$ (c 1.0, CHCl$_3$). $\nu_{max}$ (CHCl$_3$): 3370, 1795, 1695 cm$^{-1}$. $\delta$(CDCl$_3$): 2.40 (1H, br.s, OH), 2.65 (2H, t, J 6 Hz), 2.95 (1H, d, J 16 Hz), 3.15–3.80 (6H, complex), 4.25–4.55 (2H, complex), 5.47 (1H, d, J 2 Hz). m/e: 138 (67%), 96 (100).

EXAMPLE 9

(Z)-(5R)-3-[2-(p-Hydroxyphenylthio)ethylidene]-4-oxa-1-azabicyclo[3.2.0]heptan-7-one (5R)-7-Oxo-3-vinyl-4-oxa-1-azabicyclo[3.2.0] hept-2-ene (2.5 mmole) in dry tetrahydrofuran (20 ml) was treated with p-mercaptophenol (650 mg) and benzoyl peroxide (10 mg). The resulting solution was stirred under dry nitrogen while being irradiated using a 200 W bulb placed 1″ from the reaction vessel for 1 hour. (The temperature of the solution was 25°–30° during this period). The mixture was diluted with ethyl acetate (100 ml) and was washed with water (3×30 ml) and saturated brine (30 ml). The solution was dried (magnesium sulphate) and the solvent was evaporated under reduced pressure to yield a pale yellow gum. The gum was chromatographed on silica gel using ethyl acetate/petroleum ether (b.p. 60°–80°) to give the title compound as a colourless waxy solid (125 mg), $[\alpha]_D^{20} = +138.5°$ (c 1.0, CHCl$_3$), (Found: M$^+$, 263.0585; C$_{13}$H$_{13}$NO$_3$S requires 263.0616). $\nu_{max}$ (CHCl$_3$): 3200, 1790, 1695, 1600, 1580, 1495 cm$^{-1}$. $\delta$ (CDCl$_3$): 2.62 (1H, d, J 16 Hz), 3.10–3.65 (4H, complex), 4.24 (1H, d, J 14 Hz), 4.39 (1H, t, J 7 Hz), 5.25 (1H, d, J 2 Hz), 6.5–6.8 (3H, m), 7.15–7.35 (2H, m). m/e: 263 (M$^+$, 9%), 138 (100), 126 (25), 125 (23), 96 (42).

EXAMPLE 10

(Z)-(5R)-3-[2-(p-Acetamidophenylthio)ethylidene]-4-oxa-1-azabicyclo[3.2.0]heptan-7-one

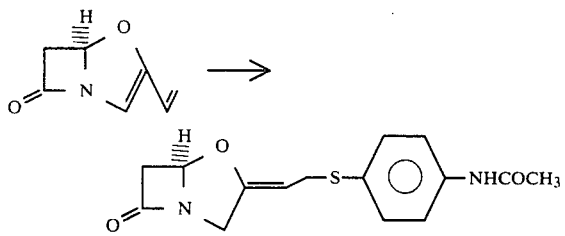

(5R)-7-Oxo-3-vinyl-4-oxa-1-azabicyclo[3.2.0]hept-2-ene (2.6 mmole) and p-acetamidophenyl mercaptan (0.5 g) were converted into the title compound using the process described in Example 1. The title compound was obtained as a colourless gum (102 mg), $[\alpha]_D^{25} = +39.3°$ (c 1.0, CHCl$_3$), (Found: M+; 304.0896; $C_{15}H_{16}N_2O_3S$ requires 304.0882). $\nu_{max}$ (CHCl$_3$): 3380, 3280, 1790, 1720, 1690 (sh), 1665, 1590, 1496 cm$^{-1}$. $\delta$(CDCl$_3$): 2.08 (3H, s), 2.60–3.50 (5H, complex), 4.18 (1H, d, J 14 Hz), 4.35 (1H, t, J 7 Hz), 5.30 (1H, d, J 2 Hz), 7.10–7.40 (4H, complex), 7.80 (1H, br.s). m/e: 304 (M+, 12%), 138 (100), 96 (62).

EXAMPLE 11

(Z)-(5R)-3-[2-(p-Benzyloxycarbonylaminophenylthio)ethylidene]-4-oxa-1-azabicyclo[3.2.0]heptan-7-one

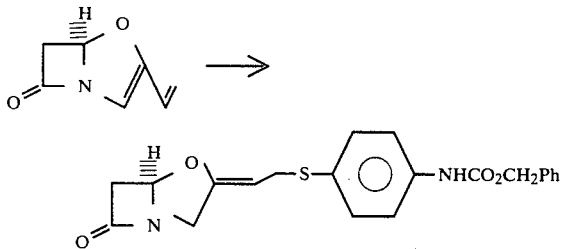

(5R)-7-Oxo-3-vinyl-4-oxa-1-azabicyclo[3.2.0]hept-2-ene (2.4 mmole) and p-benzyloxycarbonylaminophenyl mercaptan (0.775 g) were converted into the title compound using the process described in Example 1. The title compound was obtained as a colourless gum (63 mg), $[\alpha]_D^{25} = 34.6°$ (c 1.0, CHCl$_3$), (Found: M+, 396.1136; $C_{21}H_{20}N_2O_4S$ requires 396.1144). $\nu_{max}$ (CHCl$_3$): 3370, 3240, 1790, 1735, 1700, 1590, 1515 cm$^{-1}$. $\delta$(CDCl$_3$): 2.71 (1H, d, J 16 Hz), 3.10–3.60 (4H, complex), 4.22 (1H, d, J 15 Hz), 4.38 (1H, t, J 7 Hz), 5.16 (2H, s), 5.32 (1H, d, J 2 Hz), 6.90 (1H, br.s), 7.10–7.45 (9 H, complex). m/e: 396 (M+, 6%), 138 (41), 108(20), 107(12), 96(46), 91(100).

EXAMPLE 12

(Z)-(5R)-3-[2-(p-Acetamidophenylsulphonyl)ethylidene]-4-oxa-1-azabicyclo[3.2.0]heptan-7-one

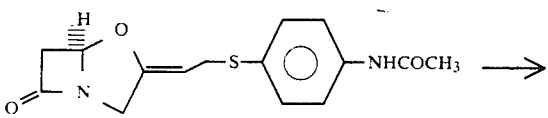

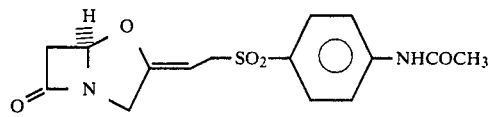

(Z)-(5R)-3-[2-(p-Acetamidophenylthio)ethylidene]-4-oxa-1-azabicyclo [3.2.0]heptan-7-one (70 mg) was dissolved in dry methylene dichloride (6 ml) and the solution was stirred and ice-cooled while m-chcloroperbenzoic acid (50 mg) in dry methylene dichloride (4 ml) was added dropwise over 5 minutes. After addition was complete, the mixture was stirred and ice-cooled for a further 25 minutes. The mixture was diluted with ethyl acetate (50 ml) and was washed with dilute sodium bicarbonate solution (30 ml) and saturated brine (30 ml). The solution was dried (magnesium sulphate) and the solvent was evaporated under reduced pressure to give a colourless gum. The gum was chromatographed on silica gel using ethyl acetate/petroleum ether (b.p. 60°–80°) to give the title compound as colourless crystals, m.p. 110°–111°, $[\alpha]_D^{20} = +40.0°$ (c 1.0, CHCl$_3$). $\nu_{max}$ (CHCl$_3$): 3390, 3250, 1790, 1690, 1585, 1505, 1315, 1140 cm$^{-1}$.

EXAMPLE 13

(Z)-(5R)-3-[2-(Methoxycarbonylmethylsulphonyl)ethylidene]-4-oxa-1-azabicyclo[3.2.0]heptan-7-one.

(Z)-(5R)-3-[2-(Methoxycarbonylmethylthio)ethylidene]-4-oxa-1-azabicyclo[3.2.0]heptan-7-one (35 mg) was oxidised using m-chloroperbenzoic acid (50 mg) by analogy with the process described in Example 12.

The title compound was obtained as a colourless gum (14 mg), $[\alpha]_D^{20} = +24.0°$ (c 1.0, CHCl$_3$). $\nu_{max}$ (CHCl$_3$): 1790, 1735, 1695, 1320, 1110 cm$^{-1}$. $\delta$(CHCl$_3$): 3.02 (1H, d, J 16 Hz), 3.45 (1H, dd, J 16 and 2 Hz), 3.64 (1H, d, J 15 Hz), 3.78 (3H, s), 3.90 (2H, s), 4.00 (2H, d, J 8 Hz), 4.45 (1H, d, J 15 Hz), 4.59 (1H, t, J 8 Hz), 5.56 (1H, d, J 2 Hz). m/e: 138 ($C_7H_8NO_2$, 90%), 131 (44), 96 ($C_5H_6NO$, 100%).

EXAMPLE 14

(Z)-(5R)-3-[2-(2-Hydroxyethylsulphonyl)ethylidene]-4-oxa-1-azabicyclo[3.2.0]heptan-7-one

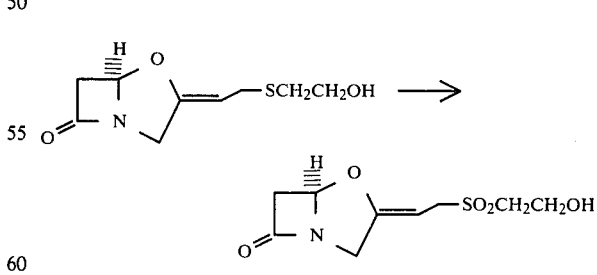

(Z)-(5R)-3-[2-(2-Hydroxyethylthio)ethylidene]-4-oxa-1-azabicyclo[3.2.0]heptan-7-one (35 mg) and m-chloroperbenzoic acid (60 mg) were converted into the title compound using the process described in Example 12. The title compound was obtained as a colourless gum (6 mg). $\nu_{max}$ (CHCl$_3$): 3450, 1795, 1700, 1315, 1110 cm$^{-1}$.

EXAMPLE 15

(Z)-(4R)-3-[2-(p-Hydroxyphenylsulphonyl)ethylidene]-4-oxa-1-azabicyclo[3.2.0]heptan-7-one

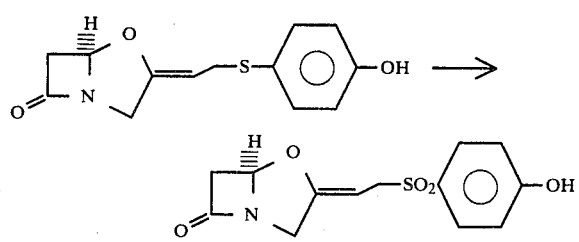

(Z)-(5R)-3-[2(p-Hydroxyphenylthio)ethylidene]-4-oxa-1-azabicyclo[3.2.0]heptan-7-one (70 mg) and m-chloroperbenzoic acid (110 mg) were converted into the title compound using the process described in Example 12. The title compound was obtained as a colourless gum (33 mg), $[\alpha]_D^{20} = +133.1°$ (c 1.0, $CHCl_3$). $\nu_{max}$ ($CHCl_3$): 3200, 1795, 1700, 1600, 1585, 1500, 1310, 1140 $cm^{-1}$.

EXAMPLE 16

Anti-fungal Activity

The anti-fungal activity of the compound of Example 7 was investigated using a microtitre method, with glucosepeptone broth at 1/50 and 1/500 final dilutions of inoculum. The organisms used were *Candida albicans* and *Saccharomyces cerevisiae*.

The minimum inhibitory concentrations (MIC) are shown below.

|  | *C. albicans* |  | *S. cerevisisae* |  |
| --- | --- | --- | --- | --- |
| Final Dilution | 1/50 | 1/500 | 1/50 | 1/500 |
| MIC (μg/ml) | 12.5 | 12.5 | >100 | 100 |

I claim:

1. A compound of the formula (II):

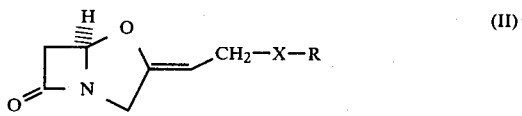

wherein X is S, SO or $SO_2$ and R is $-CH_2CO_2R^2$, $-CH_2-CH_2-R^3$ or $R^4$ wherein $R^2$ is a pharmaceutically acceptable salting ion, alkyl of up to 4 carbon atoms or benzyl, $R^3$ is $OR^1$, $NHR^1$, $NH.COR^1$ or $CO_2R^2$ wherein $R^1$ is hydrogen, alkyl of up to 4 carbon atoms or benzyl $R^2$ is as above defined and $R^4$ is thienyl, furyl, pyridyl, phenyl, or phenyl mono-substituted by fluorine, chlorine, bromine, methyl, $OR^1$, $NHR^1$, $NH.COR^1$ or $CO_2R^2$ wherein $R^1$ and $R^2$ are as above defined.

2. The compound according to claim 1 of the formula:

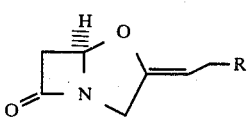

wherein R is $SC_6H_5$.

3. The compound according to claim 1 of the formula:

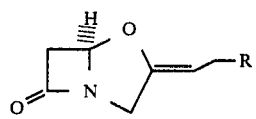

wherein R is $SO_2C_6H_5$.

4. The compound according to claim 1 of the formula:

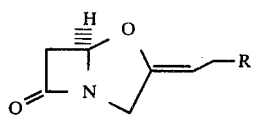

wherein R is $SOC_6H_5$.

5. The compound according to claim 1 which is (Z, 5R)-3-(2-ethylthioethylidene)-4-oxa-1-azabicyclo[3,2.0]heptan-7-one.

6. The compound according to claim 1 which is (Z)-(5R)-3-[2-methoxycarbonylmethylthio)ethylidene]-4-oxa-1-azabicyclo[3.2.0] heptan-7-one.

7. The compound according to claim 1 which is (Z)-(5R)-3-[2-(2-methoxycarbonylethylthio)ethylidene]-4-oxa-1-azabicyclo[3.2.0]heptan-7-one.

8. The compound according to claim 1 which is (Z)-(5R)-3-[2-(2-hydroxyethylthio)ethylidene]-4-oxa-1-azabicyclo[3.2.0]heptan-7-one.

9. The compound according to claim 1 which is (Z)-(5R)-3-[2-(p-hydroxyphenylthio)ethylidene]-4-oxa-1-azabicyclo[3.2.0]heptan-7-one.

10. The compound according to claim 1 which is (Z)-(5R)-3-[2-(p-acetamidophenylthio)ethylidene]-4-oxa-1-azabicyclo[3.2.0]heptan-7-one.

11. The compound according to claim 1 which is (Z)-(5R)-3-[2-(p-acetamidophenylsulphonyl)ethylidene]-4-oxa-1-azabicyclo[3.2.0]heptan-7-one.

12. The compound according to claim 1 which is (Z)-(5R)-3-[2-(2-hydroxyethylsulphonyl)ethylidene]-4-oxa-1-azabicyclo[3.2.0]heptan-7-one.

13. The compound according to claim 1 which is (Z)-(4R)-3-[2-(p-hydroxyphenylsulphonyl)ethylidene]-4-oxa-1-azabicyclo[3.2.0]heptan-7-one.

14. A compound of the formula (II):

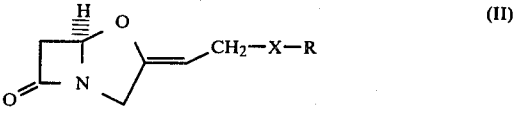

wherein X is S, SO or $SO_2$ and R is alkyl of up to 4 carbon atoms substituted by $OR^1$, $NHR^1$, $NH.COR^1$ or $CO_2R^2$ wherein $R^1$ is hydrogen or methyl and $R^2$ is a pharmaceutically acceptable salting ion.

15. A compound of the formula (II):

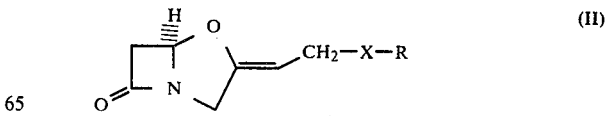

wherein X is S, SO or $SO_2$ and R is phenyl, pyridyl, furyl or thienyl.

16. A compound of the formula (II):

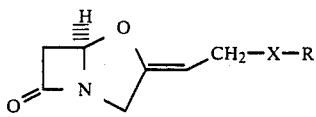

wherein X is S, SO or $SO_2$ and R is methyl, ethyl, n-propyl, n-butyl, benzyl, phenyl, methoxyphenyl of methoxybenzyl.

17. A compound of the formula (II)

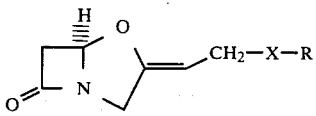

wherein X is S, SO or $SO_2$ and R is phenyl unsubstituted or mon-substituted by fluorine, chlorine, bromine, methyl, $OR^1$, $NHR^1$, $NH.CO.R^1$ or $CO_2R^2$ wherein $R^1$ is hydrogen, alkyl of up to 4 carbon atoms or benzyl and $R^2$ is a pharmaceutically acceptable salting ion, alkyl of up to 4 carbon atoms or benzyl.

18. A method of treating fungal infections in humans and mammals which comprises administering to a human or mammal in need thereof an anti-fungally effective amount of a compound of the formula (II):

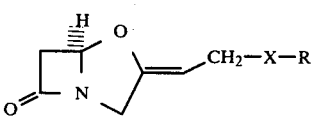

wherein X is S, SO and $SO_2$; and R is alkyl of up to 4 carbon atoms substituted by $OR^1$, $NMR^1$, $NH.CO.R^1$ or $CO_2R^2$ wherein $R^1$ is hydrogen or methyl, and $R^2$ is a pharmaceutically acceptable salting ion, in combination with a pharmaceutically acceptable carrier.

19. A method of treating fungal infections in humans and mammals which comprises administering to a human or mammal in need thereof an anti-fungally effective amount of a compound of the formula (II):

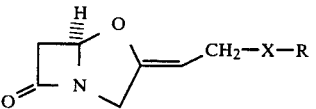

wherein X is S, SO or $SO_2$; and R is phenyl, pyridyl, furyl or thienyl, in combination with a pharmaceutically acceptable carrier.

20. A method of treating fungal infections in humans and mammals which comprises administering to a human or mammal in need thereof an anti-fungally effective amount of a compound of the formula (II):

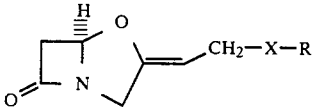

or a pharmaceutically acceptable salt thereof wherein X is S, SO or $SO_2$; and R is methyl, ethyl, n-propyl, n-butyl, benzyl, phenyl, methoxyphenyl or methoxybenzyl, in combination with a pharmaceutically acceptable carrier.

21. A method of treating fungal infections in humans and mammals which comprises administering to a human or mammal in need thereof an anti-fungally effective amount of a compound of the formula (II):

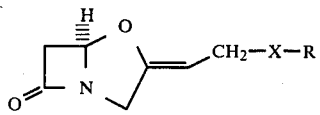

or a pharmaceutically acceptable salt thereof wherein X is S, SO or $SO_2$; and R is phenyl unsubstituted or monosubstituted by fluorine, chlorine, bromine, methyl, $OR^1$, $NHR^1$, $NH.COR^1$ or $CO_2R^2$ wherein $R^1$ is hydrogen alkyl of up to 4 carbon atoms or benzyl and $R^2$ is a pharmaceutically acceptable salting ion, alkyl of up to 4 carbon atoms or benzyl, in combination with a pharmaceutically acceptable carrier.

22. A method of treating fungal infections in humans and mammals which comprises administering to a human or mammal in need thereof an anti-fungally effective amount of (Z, 5R)-3-(2-ethylthioethylidene)-4-oxa-1-azabicyclo[3,2.0]heptan-7-one, in combination with a pharmaceutically acceptable carrier.

23. A method according to claim 18 wherein the compound is (Z)-(5R)-3-[2-methoxycarbonylmethylthio)ethylidene]-4-oxa-1-azabicyclo[3.2.0]heptan-7-one.

24. A method according to claim 18 wherein the compound is (Z)-(5R)-3-[2-(2-methoxycarbonylethylthio)ethylidene]-4-oxa-1-azabicyclo[3.2.0]heptan-7-one.

25. A method according to claim 18 wherein the compound is (Z)-(5R)-3-[2-(2-hydroxyethylthio)ethylidene]-4-oxa-1-azabicyclo[3.2.0]heptan-7-one.

26. A method according to claim 18 wherein the compound is (Z)-(5R)-3-[2-(p-hydroxyphenylthio)ethylidene]-4-oxa-1-azabicyclo[3.2.0]heptan-7-one.

27. A method according to claim 18 wherein the compound is (Z)](5R)-3-[2-(p-acetamidophenylthio)ethylidene]-4-oxa-1-azabicyclo[3.2.0]heptan-7-one.

28. A method according to claim 18 wherein the compound is (Z)-(5R)-3-[2-(p-acetamidophenylsulphonyl)ethylidene]-4-oxa-1-azabicyclo[3.2.0]heptan-7-one.

29. A method according to claim 18 wherein the compound is (Z)-(5R)-3-[2-(2-hydroxyethylsulphonyl)ethylidene]-4-oxa-1-azabicyclo[3.2.0]heptan-7-one.

30. A method according to claim 18 wherein the compound is (Z)-(4R)-3-[2-(p-hydroxyphenylsulphonyl)ethylidene]-4-oxa-1-azabicyclo[3.2.0]heptan-7-one.

31. A method according to claim 18 wherein the compound is administered in the form of a pharmaceutically acceptable salt wherein said salt is the sodium, potassium, calcium, magnesium, ammonium, trimethylammonium, pyrroldinium salt.

32. A salt of the formula (II):

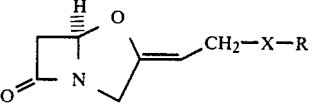

wherein X is S, SO or $SO_2$ and R is $-CH_2CO_2R^2$ wherein $R^2$ is a lithium ion.

33. A method according to claim 21 wherein the compound is of the formula:

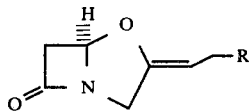

wherein R is SC$_6$H$_5$.

34. A method according to claim 21 wherein the compound is of the formula:

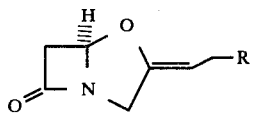

wherein R is SO$_2$C$_6$H$_5$.

35. A method according to claim 21 wherein the compound is of the formula:

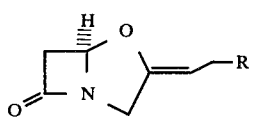

wherein R is SOC$_6$H$_5$.

36. A method according to claim 18 in oral administration form.

37. A method according to claim 18 in parenteral administration form.

38. A method according to claim 18 in rectal administration form.

39. A method according to claim 18 in intravaginal administration form.

40. A method according to claim 19 in oral administration form.

41. A method according to claim 19 in parenteral administration form.

42. A method according to claim 19 in rectal administration form.

43. A method according to claim 19 in intravaginal administration form.

44. A method according to claim 20 in oral administration form.

45. A method according to claim 20 in parenteral administration form.

46. A method according to claim 20 in rectal administration form.

47. A method according to claim 20 in intravaginal administration form.

48. A method according to claim 21 in oral administration form.

49. A method according to claim 21 in parenteral administration form.

50. A method according to claim 21 in rectal administration form.

51. A method according to claim 21 in intravaginal administration form.

52. A compound according to claim 1 wherein the pharmaceutically acceptable salt is the sodium, potassium, calcium, magnesium, ammonium, trimethylammonium or pyrrolidinium salt.

* * * * *